(12) United States Patent
Clark et al.

(10) Patent No.: US 7,777,087 B2
(45) Date of Patent: Aug. 17, 2010

(54) LIQUID PHASE ALKYLATION WITH MULTIPLE CATALYSTS

(75) Inventors: Michael C. Clark, Chantilly, VA (US); Vijay Nanda, Houston, TX (US); Chung-Ming Chi, Needham, MA (US); Maruti Bhandarkar, East Weymouth, MA (US); Brian Maerz, Chelmsford, MA (US); Matthew J. Vincent, Baytown, TX (US)

(73) Assignees: ExxonMobil Chemical Patents Inc., Houston, TX (US); Stone & Webster, Inc., Houston, TX (US)

( * ) Notice: Subject to any disclaimer, the term of this patent is extended or adjusted under 35 U.S.C. 154(b) by 0 days.

(21) Appl. No.: 12/624,118

(22) Filed: Nov. 23, 2009

(65) Prior Publication Data

US 2010/0069693 A1     Mar. 18, 2010

Related U.S. Application Data

(63) Continuation of application No. 11/655,452, filed on Jan. 19, 2007.

(51) Int. Cl.
*C07C 2/66* (2006.01)
(52) U.S. Cl. ...................... 585/449; 585/467
(58) Field of Classification Search ................ 585/449, 585/467
See application file for complete search history.

(56) References Cited

U.S. PATENT DOCUMENTS

| 3,751,504 A | 8/1973 | Keown et al. |
|---|---|---|
| 3,751,506 A | 8/1973 | Burress |
| 3,755,483 A | 8/1973 | Burress |
| 4,891,458 A | 1/1990 | Innes et al. |
| 4,992,606 A | 2/1991 | Kushnerick et al. |
| 5,149,894 A | 9/1992 | Holtermann et al. |
| 5,258,565 A | 11/1993 | Kresge et al. |
| 5,371,310 A | 12/1994 | Bennett et al. |
| 5,453,554 A | 9/1995 | Cheng et al. |
| 5,955,642 A | 9/1999 | Merrill et al. |
| 5,998,687 A | 12/1999 | Woodle et al. |
| 6,057,485 A | 5/2000 | Merrill et al. |
| 6,077,498 A | 6/2000 | Diaz Cabanas et al. |
| 6,090,991 A | 7/2000 | Butler et al. |
| 6,231,751 B1 | 5/2001 | Canos et al. |
| 6,232,515 B1 | 5/2001 | Schulz et al. |
| 6,995,295 B2 | 2/2006 | Clark et al. |
| 7,071,369 B2 | 7/2006 | Pohl |
| 2002/0042548 A1 | 4/2002 | Dandekar et al. |
| 2004/0220438 A1 | 11/2004 | Chen et al. |

FOREIGN PATENT DOCUMENTS

| EP | 0 432 814 | 6/1991 |
|---|---|---|
| EP | 0 629 549 | 12/1994 |
| WO | 2006/107471 | 10/2006 |
| WO | 2007/130054 | 11/2007 |
| WO | 2007/130055 | 11/2007 |

*Primary Examiner*—Thuan Dinh Dang
(74) *Attorney, Agent, or Firm*—Darryl M. Tyus; Xiaobing Feng

(57) ABSTRACT

A process is disclosed for producing an alkylaromatic compound in a multistage reaction system comprising at least first and second series-connected alkylation reaction zones, each containing an alkylation catalyst. A first feed comprising an alkylatable aromatic compound and a second feed comprising an alkene are introduced into the first alkylation reaction zone. The first and second alkylation reaction zones are operated under conditions of temperature and pressure effective to cause alkylation of the aromatic compound with the alkene in the presence of the alkylation catalyst, the temperature and pressure being such that the aromatic compound is at least partly in the liquid phase. The alkylation catalyst in the first alkylation reaction zone, which may be a reactor guard bed, has more acid sites per unit volume of catalyst than the alkylation catalyst in the second reaction zone.

17 Claims, 1 Drawing Sheet

LIQUID PHASE ALKYLATION WITH MULTIPLE CATALYSTS

CROSS REFERENCE TO RELATED APPLICATIONS

This application is a Continuation Application of U.S. application Ser. No. 11/655,452, filed Jan. 19, 2007, now allowed.

FIELD

The present disclosure relates to a process for producing alkylaromatic compounds, particularly ethylbenzene.

BACKGROUND

Ethylbenzene is a key raw material in the production of styrene and is produced by the reaction of ethylene and benzene in the presence of an acid catalyst. Old ethylbenzene production plants, typically built before 1980, used $AlCl_3$ or $BF_3$ as the acidic catalyst. Newer plants have in general been switching to zeolite-based acidic catalysts.

Traditionally, ethylbenzene has been produced in vapor-phase reactor systems, in which the ethylation reaction of benzene with ethylene is carried out at a temperature of about 380-420° C. and a pressure of 9-15 $kg/cm^2$-g in multiple fixed beds of zeolite catalyst. Ethylene exothermally reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and heavier aromatic products. All these chain reaction products are commonly referred as polyethylated benzenes (PEBs). In addition to the ethylation reactions, the formation of xylene isomers as trace products occurs by side reactions. This xylene formation in vapor phase processes may yield an ethylbenzene product with about 0.05-0.20 wt % of xylenes. The xylenes show up as an impurity in the subsequent styrene product, and are generally considered undesirable.

In order to minimize the formation of PEBs, a stoichiometric excess of benzene, about 400-900% per pass, is applied, depending on process optimization. The effluent from the ethylation reactor contains about 70-85 wt % of unreacted benzene, about 12-20 wt % of ethylbenzene product and about 3-4 wt % of PEBs. To avoid a yield loss, the PEBs are converted back to ethylbenzene by transalkylation with additional benzene, normally in a separate transalkylation reactor.

By way of example, vapor phase ethylation of benzene over the crystalline aluminosilicate zeolite ZSM-5 is disclosed in U.S. Pat. Nos. 3,751,504 (Keown et al.), 3,751,506 (Burress), and 3,755,483 (Burress).

In recent years the trend in industry has been to shift away from vapor phase reactors to liquid phase reactors. Liquid phase reactors operate at a temperature of about 170-250° C., which is below the critical temperature of benzene (about 290° C.). One advantage of the liquid phase reactor is the very low formation of xylenes and other undesirable byproducts. The rate of the ethylation reaction is normally lower compared with the vapor phase, but the lower design temperature of the liquid phase reaction usually economically compensates for the negatives associated with the higher catalyst volume. Thus, due to the kinetics of the lower ethylation temperatures, resulting from the liquid phase catalyst, the rate of the chain reactions forming PEBs is considerably lower; namely, about 5-8% of the ethylbenzene is converted to PEBs in liquid phase reactions versus the 15-20% converted in vapor phase reactions. Hence the stoichiometric excess of benzene in liquid phase systems is typically 150-400%, compared with 400-900% in vapor phase.

Liquid phase ethylation of benzene using zeolite beta as the catalyst is disclosed in U.S. Pat. No. 4,891,458 and European Patent Publication Nos. 0432814 and 0629549. More recently it has been disclosed that MCM-22 and its structural analogues have utility in these alkylation/transalkylation reactions, see, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); and U.S. Pat. No. 6,231,751 (ITQ-2).

Commercial liquid phase ethylbenzene manufacturing processes generally employ a plurality of series-connected alkylation reaction zones, each containing a bed of alkylation catalyst. Most, if not all, of the benzene is normally fed to a first inlet reaction zone, whereas the ethylene feed is typically divided substantially equally between the reaction zones. Poisons can and do enter the alkylation reaction system with both the ethylene and benzene feeds and the alkylation system frequently includes a by-passable reactive guard bed, which is normally located in a pre-reactor separate from the remainder of the alkylation system. The reactive guard bed is also loaded with alkylation catalyst and is maintained under ambient or up to alkylation conditions. Benzene and at least a portion of the ethylene are passed through the reactive guard bed prior to entry into the inlet zone of the series-connected alkylation reaction zones. The reactive guard bed not only serves to effect the desired alkylation reaction but is also used to remove any reactive impurities in the feeds, such as nitrogen compounds, which could otherwise poison the remainder of the alkylation catalyst.

By virtue of the poisons in the benzene and ethylene feeds, the catalyst in the reactive guard bed, or where there is no reactive guard bed, the catalyst in the inlet alkylation reaction zone, is subject to more rapid deactivation, and hence requires more frequent regeneration and/or replacement, than the remainder of alkylation catalyst. To reduce the cost and potential lost production time involved in this regeneration and/or replacement, there is significant interest in developing alkylation processes which maximize the cycle length of the catalyst in the reactive guard bed and/or the inlet alkylation reaction zone.

Although the preceding discussion has focused on the production of ethylbenzene, it will be appreciated that similar comments apply to the production of other alkylaromatic compounds, such as cumene and sec-butylbenzene, in which the alkylating group comprises other lower ($C_2$-$C_5$) alkenes, such as propylene and 1-butene and/or 2-butene.

The present disclosure provides an aromatics alkylation process that allows the use of a catalyst in the reactive guard bed or the inlet bed (first alkylation reaction zone) which exhibits an increased poison capacity (on a moles of poison per unit mass of catalyst basis), as a result of which the reactive guard bed or the inlet bed exhibits an increased cycle length between catalyst change-outs. This can be accomplished by providing an alkylation catalyst in the reactive guard bed or the inlet bed which has a greater amount of acid sites per unit mass of the catalyst than the alkylation catalyst in the second bed (second alkylation reaction zone).

U.S. Pat. No. 5,998,687 discloses a process for producing ethylbenzene comprising: a) contacting a first feed comprising benzene and ethylene with a first catalyst comprising zeolite beta in a first catalyst zone at first alkylation conditions to obtain a first effluent, and withdrawing the first effluent from the first catalyst zone at a first temperature; and b)

contacting a second feed including at least a portion of the first effluent and comprising ethylene and benzene with a second catalyst comprising zeolite Y in a second catalyst zone at second alkylation conditions to obtain a second effluent comprising ethylbenzene, and withdrawing the second effluent from the second catalyst zone at a second temperature, wherein the second temperature is higher than the first temperature.

U.S. Pat. No. 6,057,485 discloses a process for producing ethylbenzene by gas-phase alkylation over a split load of monoclinic silicalite alkylation catalysts having different silica/alumina ratios. A feedstock containing benzene and ethylene is applied to a multi-stage alkylation reaction zone having a plurality of series-connected catalyst beds. At least one catalyst bed contains a first monoclinic silicalite catalyst having a silica/alumina ratio of at least 275 and at least one other catalyst bed contains a second monoclinic silicalite catalyst having a silica/alumina ratio of less than about 275. The alkylation reaction zone is operated at temperature and pressure conditions in which the benzene is in the gaseous phase to cause gas-phase alkylation of the aromatic substrate in the presence of the monoclinic silicalite catalysts to produce an alkylation product. The alkylation product is then withdrawn from the reaction zone for separation and recovery. The use of the split load of catalyst is said to allow a higher purity ethylbenzene product to be produced at improved efficiencies than if only one of the catalysts were used by itself.

U.S. Pat. No. 6,995,295 discloses a process for producing an alkylaromatic compound by reacting an alkylatable aromatic compound with a feed comprising an alkene and an alkane in a multistage reaction system comprising a plurality of series-connected alkylation reaction zones each containing an alkylation catalyst. The process comprises: (a) operating at least one of said alkylation reaction zones under conditions of temperature and pressure effective to cause alkylation of said aromatic compound with said alkene in the presence of said alkylation catalyst and to maintain said temperature and pressure being such that part of said aromatic compound is in the vapor phase and part is in the liquid phase; (b) withdrawing from said one alkylation reaction zone an effluent comprising said alkylaromatic compound, unreacted alkylatable aromatic compound, any unreacted alkene and said alkane; (c) removing at least part of said alkane from said one alkylation reaction zone effluent to produce an alkane-depleted effluent; and (d) supplying said alkane-depleted effluent to another of said alkylation reaction zones. The process may employ a by-passable reactive guard bed which is located in a prereactor separate from the remainder of the alkylation system and which is loaded with alkylation catalyst, which may be the same of different from the catalyst used in the alkylation reaction zones.

SUMMARY

In one aspect, the present disclosure resides in a process for producing an alkylaromatic compound, the process comprising:

(a) introducing a first feed comprising an alkylatable aromatic compound and a second feed comprising an alkene into a first alkylation reaction zone comprising a first alkylation catalyst, wherein the first alkylation catalyst has a first amount of acid sites per unit mass of the catalyst;

(b) operating said first alkylation reaction zone under conditions effective to cause alkylation of said alkylatable aromatic compound by said alkene to produce said alkylaromatic compound, said conditions being such that said alkylatable aromatic compound is at least partly in the liquid phase;

(c) withdrawing from said first alkylation reaction zone a first effluent comprising said alkylaromatic compound and unreacted alkylatable aromatic compound;

(d) introducing at least part of said first effluent and a third feed comprising said alkene into a second alkylation reaction zone comprising a second alkylation catalyst, wherein the second alkylation catalyst has a second amount of acid sites per unit mass of the catalyst and wherein said second amount is less than said first amount;

(e) operating said second alkylation reaction zone under conditions effective to cause alkylation of said unreacted alkylatable aromatic compound by said alkene to produce said alkylaromatic compound, said conditions being such that said alkylatable aromatic compound is at least partly in the liquid phase; and (f) withdrawing from said second alkylation reaction zone a second effluent comprising said alkylaromatic compound.

In one embodiment, each of said first and second alkylation catalysts comprises an aluminosilicate molecular sieve and the silica to alumina molar ratio of the first alkylation catalyst is less than the silica to alumina molar ratio of the second alkylation catalyst.

Conveniently, each of said first and second alkylation catalysts comprises a molecular sieve selected from zeolite beta, zeolite Y, Ultrastable Y (USY) and a zeolite of the MCM-22 family. In one embodiment, said first alkylation catalyst comprises MCM-49 and said second alkylation catalyst comprises MCM-22.

In another embodiment, each of said first and second alkylation catalysts further comprises a binder and the weight ratio of the binder to the molecular sieve in the first alkylation catalyst is less than the weight ratio of the binder to the molecular sieve in the second alkylation catalyst.

Conveniently, the first and second alkylation reaction zones are contained within the same alkylation reactor. Alternatively, the first alkylation reaction zone is a by-passable guard bed reactor and the second alkylation reaction zone is in a separate reactor containing at least one further alkylation reaction zone connected in series with said second alkylation reaction zone.

In one embodiment, said alkene includes ethylene, said alkylatable aromatic compound includes benzene and said alkylaromatic compound includes ethylbenzene. Conveniently, the conditions in (b) and/or (e) include a temperature of about 120° C. to about 270° C. and a pressure of about 675 kPa to about 8300 kPa.

In another embodiment, said alkene includes propylene, said alkylatable aromatic compound includes benzene and said alkylaromatic compound includes cumene. Conveniently, the conditions in (b) and/or (e) include a temperature of about 75° C. to about 250° C. and a pressure of about 1000 kPa to about 5000 kPa.

In yet another embodiment, said alkene includes 1-butene and/or 2-butene, said alkylatable aromatic compound includes benzene and said alkylaromatic compound includes sec-butylbenzene. Conveniently, the conditions in (b) and/or (e) include a temperature of about 75° C. to about 250° C. and a pressure of about 500 kPa to about 4000 kPa.

DETAILED DESCRIPTION OF THE EMBODIMENTS

Figure 1:
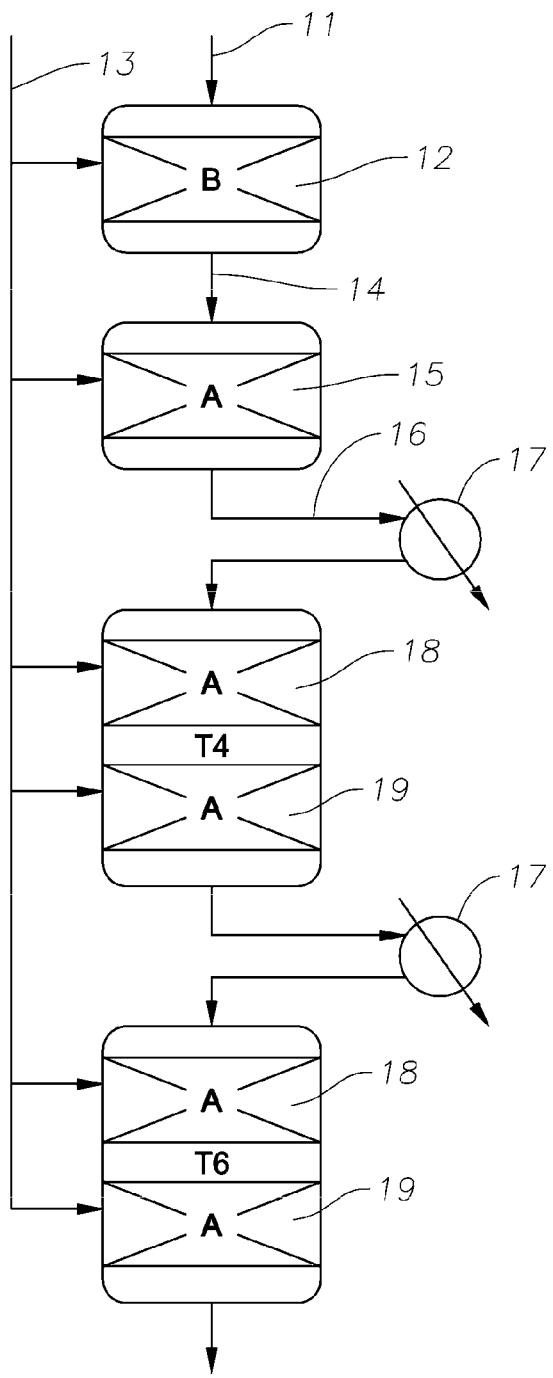
FIG. 1 is a flow diagram of a process for producing ethylbenzene in accordance with a first embodiment of the present disclosure.

The present disclosure provides an at least partly liquid phase process for producing alkylaromatic compounds from feeds of an alkylatable aromatic compound and an alkene in at least two series-connected alkylation reaction zones, preferably in a plurality of series-connected alkylation reaction zones, each containing a bed of alkylation catalyst. Typically, the alkylation reaction zones are arranged in pairs, with one or more pairs being contained within the same alkylation reactor. Generally, since the alkylation reaction is exothermic, interstage cooling is provided between adjacent pairs of reaction zones.

Frequently, the alkylation system includes a by-passable reactive guard bed in addition to, and upstream of, and in series with, either the series-connected alkylation reaction zones or at least one further alkylation reaction zone. The reactive guard bed is normally located in a pre-reactor separate from the remainder of the alkylation system. The reactive guard bed is also loaded with alkylation catalyst, which may be the same or different from the catalyst used in the series-connected, multi-stage alkylation reaction system, and is maintained under ambient or up to alkylation conditions, i.e., conditions wherein the alkylatable aromatic compound is at least partly in the liquid phase. The reactive guard bed not only serves to effect the desired alkylation reaction but is also used to remove any reactive impurities in the feeds, such as nitrogen compounds, which could otherwise poison the remainder of the alkylation catalyst. The catalyst in the guard bed is, therefore, subject to more frequent regeneration and/or replacement than the remainder of the alkylation catalyst and hence the guard bed is normally provided with a by-pass circuit so that the alkylation feedstocks may be fed directly to the series-connected alkylation reaction zones when the guard bed is out of service or where it is not desired to use the guard bed. The reactive guard bed may operate in all liquid phase or mixed phase in co-current upflow or downflow operation.

Each alkylation reaction zone is operated under conditions effective not only to cause alkylation of the aromatic compound with the alkene in the presence of the alkylation catalyst, but also to result in the aromatic compound being at least partly in the liquid phase. More particularly, as will be discussed in more detail below, the operating conditions in each alkylation reaction zone are controlled such that the alkylatable aromatic compound is either completely in the liquid phase or partly in the liquid phase and partly in the vapor phase. Unless the alkylatable aromatic compound is completely in the liquid phase, the operating conditions in each alkylation reaction zone are generally controlled so that the ratio of the volume of liquid to the volume of vapor in each reaction zone is from about 0.1 to about 10, more particularly from about 0.2 to about 5, desirably from about 0.4 to about 2.0 and, preferably from about 0.5 to about 1. In determining the liquid to vapor volume ration in a given reaction zone, the total volume of all the reactants in the liquid phase in the reaction zone is divided by the total volume of all the reactants in the vapor phase in the reaction zone.

The effluent from each alkylation reaction zone comprises the desired alkylaromatic compound, unreacted alkylatable aromatic compound, any unreacted alkene (overall alkene conversion is expected to be 98-99.99+%), and any impurities. Each alkylation reaction zone effluent, except for that from the final alkylation reaction zone, is then passed to the subsequent alkylation reaction zone where additional alkene feedstock is added for reaction with the unreacted aromatic compound.

In one embodiment of the disclosure, the series-connected, multi-stage alkylation reaction system used in the process of the disclosure is highly selective to the desired monoalkylated product, such as ethylbenzene, but normally produces at least some polyalkylated species, such as diethylbenzene. Thus the effluent from the final alkylation stage comprises the desired monoalkylated product and the polyalkylated species along with unreacted alkene (if any) and unreacted alkylated aromatic compound. This effluent is passed to separation train in which the unreacted alkene, unreacted alkylated aromatic compound, and desired monalkylated product are serially separated. The remaining polyalkylated species is fed to a transalkylation reactor, which is normally separate from the alkylation reactor, where additional monoalkylated product is produced by reacting the polyalkylated species with additional aromatic compound.

Reactants

The reactants used in the process of the disclosure include an alkylatable aromatic compound and an alkene alkylating agent.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act completely deactivate the catalyst by poisoning the catalyst under the reaction conditions selected.

Substituted aromatic compounds which may be alkylated herein must possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which may be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10- dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate or cut thereof containing substantial quantities of benzene (>1%), toluene and/or xylene constitutes a particularly useful feed for the alkylation process of this disclosure.

Suitable alkene alkylating agents useful in the process of this disclosure includes alkenes, such as ethylene, propylene, 1-butene and 2-butene, preferably ethylene.

Preferably, the reactants in the process of the disclosure are benzene and ethylene and the desired reaction product is ethylbenzene.

Alkylation Catalysts

In one embodiment, the alkylation catalyst employed in the alkylation zone(s) or the alkylation catalyst employed in each alkylation reaction zone, including the reactive guard bed, comprises at least one medium pore molecular sieve having a Constraint Index of 2-12 (as defined in U.S. Pat. No. 4,016, 218). Suitable medium pore molecular sieves include ZSM-5, ZSM-11, ZSM-12, ZSM-22, ZSM-23, ZSM-35, and ZSM-48. ZSM-5 is described in detail in U.S. Pat. No. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In another embodiment, the alkylation catalyst employed in the alkylation zone(s) or the alkylation catalyst employed in each alkylation reaction zone, including the reactive guard bed, comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250, 277), MCM-49 (described in U.S. Pat. No. 5,236,575), MCM-56 (described in U.S. Pat. No. 5,362,697), UZM-8 (described in U.S. Pat. No. 6,756,030), and mixtures thereof.

In a further embodiment, the alkylation catalyst employed in the or each alkylation reaction zone, including the reactive guard bed, comprises one or more large pore molecular sieves having a Constraint Index less than 2. Suitable large pore molecular sieves include zeolite beta, zeolite Y, Ultrastable Y (USY), Dealuminized Y (Deal Y), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293, 192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferred molecular sieves for use in the present process comprise ZSM-5, zeolite beta, zeolite Y, Ultrastable Y (USY) and zeolites of the MCM-22 family.

The above molecular sieves may be used as the alkylation catalyst in the process of the disclosure without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

Generally, the alkylatable aromatic compound and the alkene supplied to the present process will contain some level of reactive impurities, such as nitrogen compounds, which are small enough to enter the pores of the alkylation catalyst and thereby poison the catalyst. Moreover, it is normal to supply all the alkylatable aromatic compound to the first alkylation reaction zone, whether this be an entry zone of the main alkylation system or an upstream guard bed, but to divide the alkene feed between the alkylation reaction zones. Thus the catalyst in the first alkylation reaction zone is more susceptible to poisoning by impurities than that in the second and subsequent downstream reaction zones. Thus to reduce the frequency with which the catalyst in the first alkylation reaction zone must be removed for replacement, regeneration or reactivation, the present process employs a first alkylation catalyst in the first alkylation reaction zone and a second alkylation catalyst in the second alkylation reaction zone, wherein the first and second catalysts are different in that the first catalyst has a greater number of acid sites per unit mass of the catalyst than the second catalyst. Apart from the difference in the number of acid sites per unit mass of the catalyst, the first and second alkylation catalysts can employ the same or different zeolite materials.

In one embodiment, the ratio of the number of acid sites per unit mass of the first alkylation catalyst to the number of acid sites per unit mass of the second alkylation catalyst is in the range of 40:1 to 1:1, and generally in the range of 10:1 to 1:1. The number of acid sites per unit mass of a catalyst can be determined by variety of techniques including, but not limited to, Bronsted proton measurement, tetrahedral aluminum measurement, the adsorption of ammonia, pyridine and other amines, and the rate constant for the cracking of hexane. Although these techniques are disparate in nature, all provide a relative measure of the number of active sites on a fresh zeolite catalyst such as faujasite, beta, the pentasil family zeolites and the MWW (MCM-22) family zeolites. A particularly suitable method of measuring the number of acid sites per unit mass of a catalyst is pyridine sorption since pyridine is about the same size or larger than the typical poisons present in alkylation processes and pyridine is readily adsorbed by the zeolitic materials identified as suitable alkylation catalysts.

The different levels of acid sites in catalysts used in the first and second alkylation reaction zones can readily achieved by varying the level of (non-acidic) binder between the catalysts. For example, the weight ratio of the binder to the active component(s) in first alkylation catalyst in the first alkylation reaction zone can be less, or the first alkylation catalyst can be unbound, than the weight ratio of the binder to the active component(s) in the second alkylation catalyst in the second alkylation reaction zone. Alternatively, or in addition to the binder level, where the active components of the catalysts comprise aluminosilicate zeolites, the first alkylation catalyst in the first alkylation reaction zone can employ a zeolite having a lower silica to alumina molar ratio than that of the zeolite employed on the second alkylation catalyst in the second alkylation reaction zone. Thus, with aluminosilicate zeolites, the level of acid sites in a catalyst is generally a function of the amount of zeolitic aluminum in the catalyst. For example, in one embodiment, MCM-49 can be employed as an active component in the first alkylation catalyst in the first alkylation reaction zone, whereas MCM-22 is employed as an active component in the second alkylation catalyst in the second alkylation reaction zone.

In addition to the issue of catalyst poisoning, where the alkylation reaction zones are arranged in pairs with interstage cooling being provided between adjacent pairs of reaction zones, it will be appreciated that the exothermic nature of the reaction will tend to cause the downstream zone of each pair to be at a higher temperature than the upstream zone. For this reason, it may be desirable to employ a catalyst with more acid sites in the upstream zone of each pair of alkylation reaction zones than the catalyst in the downstream zone. Again this can be achieved by lowering the binder level and/or increasing the silica to alumina molar ratio of the catalyst in the upstream zone as compared with that in the downstream zone.

Reaction Conditions

In the present process of the disclosure, the alkylation reaction in each of the series-connected alkylation reaction zones takes place under at least partly liquid conditions which may be maintained throughout such zones, such that the alkylatable aromatic compound is either completely in the liquid phase or partly in the vapor phase and partly in the liquid phase. In this respect, it is to be appreciated that maintaining the alkylatable aromatic compound in the liquid phase or the ratio of the volume of liquid to the volume of vapor in a mixed phase alkylation reactor is a function of many variables, including temperature, pressure, alkene feed composition, the weight ratio of aromatics to alkene, and the number of interstage feed injection points (feed distribution among the reaction zones). Each of these variables must be understood and monitored in order to maintain the ratio of the volume of liquid to the volume of vapor at the desired level.

Particular conditions for carrying out the liquid or mixed phase alkylation of benzene with ethylene to produce ethylbenzene may include a temperature of from about 120 to about 270° C., a pressure of about 675 to about 8300 kPa, a WHSV based on ethylene of from about 0.1 to about 10 $hr^{-1}$, and a mole ratio of benzene to ethylene from about 1 to about 10.

Particular conditions for carrying out the liquid or mixed phase alkylation of benzene with propylene to produce cumene may include temperature of about 75° C. to about 250° C., a pressure of about 1000 kPa to about 5000 kPa, a WHSV based on propylene of from about 0.1 to about 10 $hr^{-1}$, and a mole ratio of benzene to propylene from about 1 to about 10.

Particular conditions for carrying out the liquid or mixed phase alkylation of benzene with 1-butene and/or 2-butene to produce sec-butylbenzene may include a temperature of about 75° C. to about 250° C., a pressure of about 500 kPa to about 4000 kPa, a WHSV based on butene of from about 0.1 to about 10 $hr^{-1}$ and a mole ratio of benzene to butene from about 1.0 to about 5.0.

Where the alkylation system includes a reactive guard bed, this may be operated under liquid phase conditions or mixed liquid/vapor phase conditions, but is preferably operated under liquid phase conditions. In the case of ethylbenzene production, the guard bed will preferably operate at a temperature between about 20 and about 270° C. and a pressure between about 675 to about 8300 kPa. In the case of cumene production, the guard bed will preferably operate at a temperature from about 25 to 180° C. and pressure from about 675 to 4000 kPa. In the case of sec-butylbenzene production, the guard bed will preferably operate at a temperature from about 50 to 250° C. and pressure from about 445 to 3550 kPa.

Transalkylation

The effluent from the present alkylation process will tend to contain polyalkylated aromatic compounds in addition to the desired monoalkylated species. Thus the effluent is to a product separation train that not only serves to remove unreacted alkylated aromatic compound, and monoalkylated product, but also separates the polyalkylated species. The polyalkylated species are then fed to a transalkylation reactor, which is normally separate from the alkylation reactor, where additional monoalkylated product is produced by reacting the polyalkylated species with additional aromatic compound in the presence of a transalkylation catalyst. Typically, the transalkylation reactor is operated under conditions such that the polyalkylated aromatic compounds and the alkylatable aromatic compound are at least predominantly in the liquid phase.

For example, suitable conditions for carrying out the liquid phase transalkylation of benzene with polyethylbenzenes may include a temperature of from about 150° C. to about 260° C., a pressure of 7000 kPa or less, a WHSV based on the weight of the total liquid feed to the reaction zone of from about 0.5 to about 100 $hr^{-1}$ and a mole ratio of benzene to polyethylbenzene of from about 1:1 to about 30:1. Particular conditions for carrying out the liquid phase transalkylation of benzene with polypropylbenzenes may include a temperature of from about 150° C. to about 300° C., a pressure of 5500 kPa or less, a WHSV based on the weight of the total liquid feed to the reaction zone of from about 0.1 to about 20.0 $hr^{-1}$ and a mole ratio of benzene to polypropylbenzene of from about 1.0 to about 10.0. Particular conditions for carrying out the liquid phase transalkylation of benzene with polybutylbenzenes may include a temperature of 100 to 300° C., a pressure of 1000 to 7000 kPa, a weight hourly space velocity of 1 to 50 $hr^{-1}$ on total feed, and a benzene to polybutylbenzene weight ratio of 1 to 10.

The transalkylation catalyst can comprise one or more of any of the molecular sieves discussed above in relation to the vapor phase alkylation system and can be used with or without a binder or matrix. Generally, however, the transalkylation catalyst is selected from zeolite beta, zeolite Y, Ultrastable Y (USY), Dealuminized Y (Deal Y), mordenite, ZSM-3, ZSM-4, ZSM-18, and ZSM-20.

A first embodiment of the present process, in which the alkylatable aromatic compound is benzene and the alkylating agent is a dilute ethylene stream, is shown in FIG. 1.

Benzene 11, after passage through a drying column (not shown) to reduce its water content, through treaters (not shown) to remove most catalyst poisons, such as nitrogen and sulfur containing organic species, and through a heat exchanger (not shown) to raise its temperature, is fed to a first alkylation reaction zone 12, which may be a reactive guard bed. The first alkylation reaction zone 12 also receives an ethylene feed 13 under pressure such that the benzene and ethylene pass cocurrently down through a bed of alkylation catalyst B in the first alkylation reaction zone 12. Alternately, the flow may be cocurrent upflow through the first alkylation reaction zone. The first alkylation reaction zone 12 typically operates at or near 100% ethylene conversion, but may operate at lower conversions so that the effluent 14 leaving the zone 12 is composed of ethylbenzenes, unreacted benzene and small amounts of impurities.

The effluent 14 is then passed to a second alkylation reaction zone 15, which contains alkylation catalyst A and which also receives the ethylene feed 13. The second alkylation reaction zone 15 also typically operates at or near 100% ethylene conversion and produces an effluent 16, which may be passed through a cooler 17 before being fed to a plurality of vertically spaced, series-connected pairs of catalyst beds 18, 19. Each bed 18, 19 also contains catalyst A and receives ethylene feed 13 such that the ethylene and the benzene-containing effluent from the zone 15 or the previous bed 18, 19 pass cocurrently down through the bed containing alkylation catalyst A. Alternately, the flow may be cocurrent upflow through the beds 18, 19. Again each bed 18, 19 is typically operated at or near to 100% ethylene conversion. A further optional cooler 17 is provided between each adjacent pair of beds 18, 19 to remove heat generated in the preceding pair of catalyst beds. Optionally, other methods of temperature controlled may be applied, such as effluent recycle or other suitable means.

Figure 2:
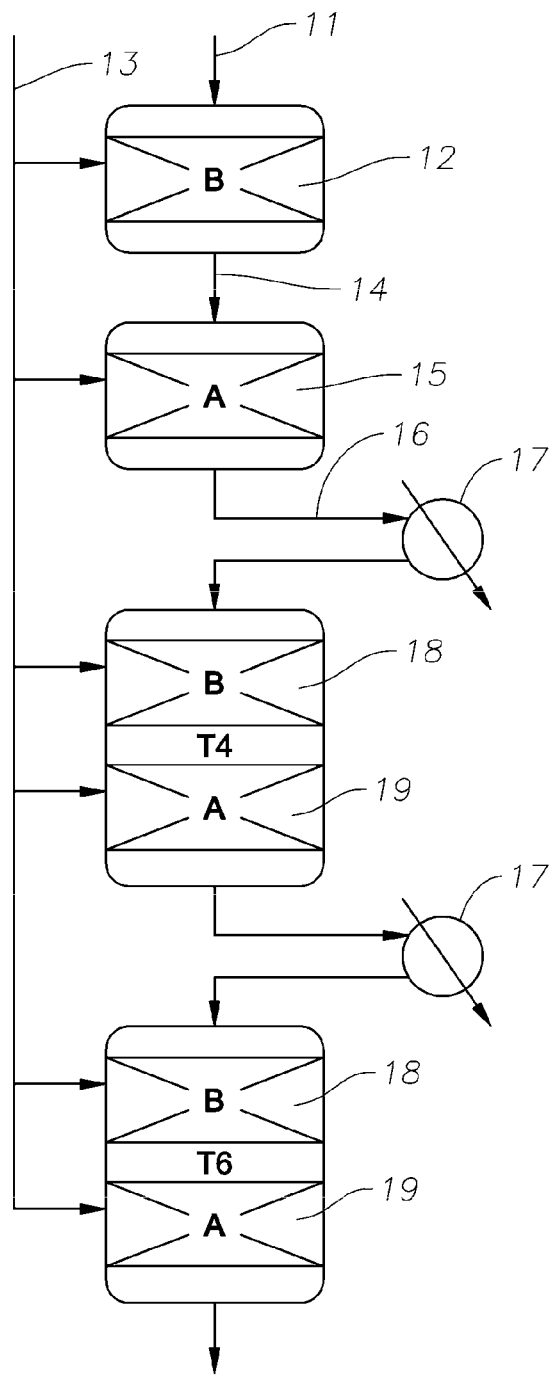
FIG. 2 is a flow diagram of a process for producing ethylbenzene in accordance with a second embodiment of the present disclosure.

In second embodiment of the disclosure, shown in FIG. 2, catalyst B having a relatively high level of acid sites is provided not only in the alkylation reaction zone 12 but also in the upstream bed 18 of each pair of catalyst beds 18, 19. Catalyst A having a relatively low level of acid sites is provided in the downstream bed 19 of each pair of catalyst beds 18, 19.

In some embodiments, this disclosure relates to:

Paragraph 1. A process for producing an alkylaromatic compound, the process comprising:
  (a) introducing a first feed comprising an alkylatable aromatic compound and a second feed comprising an alkene into a first alkylation reaction zone comprising a first alkylation catalyst, wherein the first alkylation catalyst has a first amount of acid sites per unit mass of the catalyst;
  (b) operating said first alkylation reaction zone under conditions effective to cause alkylation of said alkylatable aromatic compound by said alkene to produce said alkylaromatic compound, said conditions being such that said alkylatable aromatic compound is at least partly in the liquid phase;
  (c) withdrawing from said first alkylation reaction zone a first effluent comprising said alkylaromatic compound and unreacted alkylatable aromatic compound;
  (d) introducing at least part of said first effluent and a third feed comprising said alkene into a second alkylation reaction zone comprising a second alkylation catalyst, wherein the second alkylation catalyst has a second amount of acid sites per unit mass of the catalyst and wherein said second amount is less than said first amount;
  (e) operating said second alkylation reaction zone under conditions effective to cause alkylation of said unreacted alkylatable aromatic compound by said alkene to produce said alkylaromatic compound, said conditions being such that said alkylatable aromatic compound is at least partly in the liquid phase; and
  (f) withdrawing from said second alkylation reaction zone a second effluent comprising said alkylaromatic compound.

Paragraph 2. The process of paragraph 1, wherein each of said first and second alkylation catalysts comprises an aluminosilicate molecular sieve and the silica to alumina molar ratio of the first alkylation catalyst is less than the silica to alumina molar ratio of the second alkylation catalyst.

Paragraph 3. The process of paragraph 1 or paragraph 2, wherein each of said first and second alkylation catalysts further comprises a binder and the weight ratio of the binder to the molecular sieve in the first alkylation catalyst is less than the weight ratio of the binder to the molecular sieve in the second alkylation catalyst.

Paragraph 4. The process of any preceding paragraph, wherein said first alkylation catalyst comprises a molecular sieve selected from ZSM-5, zeolite beta, zeolite Y, Ultrastable Y (USY) and a zeolite of the MCM-22 family.

Paragraph 5. The process of any preceding paragraph, wherein said second alkylation catalyst comprises a molecular sieve selected from ZSM-5, zeolite beta, zeolite Y, Ultrastable Y (USY) and a zeolite of the MCM-22 family.

Paragraph 6. The process of any preceding paragraph, wherein said first alkylation catalyst comprises MCM-49.

Paragraph 7. The process of any preceding paragraph, wherein said second alkylation catalyst comprises MCM-22.

Paragraph 8. The process of any preceding paragraph, wherein the ratio of acid sites per unit mass of the first alkylation catalyst to acid sites per unit mass of the second alkylation catalyst is in the range of from 40:1 to 1:1.

Paragraph 9. The process of any preceding paragraph, wherein the ratio of acid sites per unit mass of the first alkylation catalyst to acid sites per unit mass of the second alkylation catalyst is in the range of from 10:1 to 1:1.

Paragraph 10. The process of any preceding paragraph, wherein the first and second alkylation reaction zones are contained within the same alkylation reactor.

Paragraph 11. The process of any one of paragraphs 1 to 9, wherein the first alkylation reaction zone is a by-passable guard bed reactor and the second alkylation reaction zone is in a separate reactor containing at least one further alkylation reaction zone connected in series with said first alkylation reaction zone.

Paragraph 12. The process of any preceding paragraph, wherein said alkene includes ethylene, said alkylatable aromatic compound includes benzene and said alkylaromatic compound includes ethylbenzene.

Paragraph 13. The process of paragraph 12, wherein said conditions in (b) and/or (e) include a temperature of about 120° C. to about 270° C. and a pressure of about 675 kPa to about 8300 kPa.

Paragraph 14. The process of any one of paragraphs 1 to 11, wherein said alkene includes propylene, said alkylatable aromatic compound includes benzene and said alkylaromatic compound includes cumene.

Paragraph 15. The process of paragraph 14, wherein said conditions in (b) and/or (e) include a temperature of about 75° C. to about 250° C. and a pressure of about 1000 kPa to about 5000.

Paragraph 16. The process of any one of paragraphs 1 to 11, wherein said alkene includes 1-butene and/or 2-butene, said alkylatable aromatic compound includes benzene and said alkylaromatic compound includes sec-butyl-benzene.

Paragraph 17. The process of paragraph 16, wherein said conditions in (b) include a temperature of about 75° C. to about 250° C. and a pressure of about 500 kPa to about 4000 kPa.

The disclosure will now be more particularly described with reference to the following Example.

EXAMPLE

A catalyst containing a MWW zeolite (for example 100% zeolite) has a measured aluminum content of 4.4 wt %. This corresponds to a Si:Al$_2$ ratio of about 18.5:1 and approximately 1.6 milliequivalents per gram of catalyst. If dried at 200° C. for 1 hr then dosed with pyridine, it was found that the uptake was 1.3 milliequivalents. This corresponds to about a 1:1 titration of a poison to available aluminum. Thus the Si:Al$_2$ ratio is a good predictor of poison capacity.

All documents described herein are incorporated by reference herein, including any priority documents and/or testing procedures to the extent they are not inconsistent with this text. While there have been described what are presently believed to be the preferred embodiments of the present disclosure, those skilled in the art will realize that other and further embodiments can be made without departing from the spirit of the disclosure, and is intended to include all such further modifications and changes as come within the true scope of the claims set forth herein.

The invention claimed is:

1. A process for producing an alkylaromatic compound, the process comprising:
    (a) introducing a first feed comprising an alkylatable aromatic compound, and a second feed comprising an alkene into a first alkylation reaction zone comprising a first alkylation catalyst having a first amount of acid sites per unit mass of the first catalyst, said first alkylation catalyst is zeolite beta or zeolite Y;
    (b) operating said first alkylation reaction zone under conditions effective to cause alkylation of said alkylatable aromatic compound by said alkene, to produce said alkylaromatic compound, said conditions being such that said alkylatable aromatic compound is at least partly in the liquid phase;
    (c) withdrawing from said first alkylation reaction zone a first effluent comprising said alkylaromatic compound and unreacted alkylatable aromatic compound;
    (d) introducing at least part of said first effluent and a third feed comprising said alkene into a second alkylation reaction zone comprising a second alkylation catalyst having a second amount of acid sites per unit mass of the second catalyst, said second alkylation is a molecular sieve having MWW topology; and
        wherein the first alkylation catalyst has a greater number of acid sites per unit mass than the second alkylation catalyst whereby the frequency at which the first alkylation catalyst is removed for replacement, regeneration or reactivation is reduced as compared to the first alkylation catalyst alone;
    (e) operating said second alkylation reaction zone under conditions effective to cause alkylation of said unreacted alkylatable aromatic compound by said alkene to produce said alkylaromatic compound, said conditions being such that said alkylatable aromatic compound is at least partly in the liquid phase; and
    (f) withdrawing from said second alkylation reaction zone a second effluent comprising said alkylaromatic compound.

2. The process of claim 1, wherein the silica to alumina molar ratio of the first alkylation catalyst is less than the silica to alumina molar ratio of the second alkylation catalyst.

3. The process of claim 2, wherein said second alkylation catalyst is selected from the group consisting of a zeolite of the MCM-22 family.

4. The process of claim 3, wherein said zeolite of the MCM-22 family is MCM-22, PSH-3, SSZ-25, ERB-1, ITQ-1, ITQ-2, MCM-36, MCM-49, MCM-56, UZM-8, and mixtures thereof.

5. The process of claim 2, wherein second alkylation catalyst comprises MCM-49.

6. The process of claim 2, wherein second alkylation catalyst comprises MCM-22 or MCM-56.

7. The process of claim 1, wherein each of said first and second alkylation catalysts further comprises a binder and the weight ratio of the binder to the molecular sieve in the first alkylation catalyst is less than the weight ratio of the binder to the molecular sieve in the second alkylation catalyst.

8. The process of claim 1, wherein the ratio of acid sites per unit mass of the first alkylation catalyst to acid sites per unit mass of the second alkylation catalyst is in the range of from about 40:1 to about 1:1.

9. The process of claim 1, wherein the ratio of acid sites per unit mass of the first alkylation catalyst to acid sites per unit mass of the second alkylation catalyst is in the range of from about 10:1 to about 1:1.

10. The process of claim 1, wherein the first and second alkylation reaction zones are contained within the same alkylation reactor.

11. The process of claim 1, wherein the first alkylation reaction zone is a by-passable guard bed reactor and the second alkylation reaction zone is in a separate reactor containing at least one further alkylation reaction zone connected in series with said first alkylation reaction zone.

12. The process of claim 1, wherein said alkene includes ethylene, said alkylatable aromatic compound includes benzene and said alkylaromatic compound includes ethylbenzene.

13. The process of claim 12, wherein said conditions in (b) and/or (e) include a temperature of about 120° C. to about 270° C. and a pressure of about 675 kPa to about 8300 kPa.

14. The process of claim 1, wherein said alkene includes propylene, said alkylatable aromatic compound includes benzene and said alkylaromatic compound includes cumene.

15. The process of claim 14, wherein said conditions in (b) and/or (e) include a temperature of about 75° C. to about 250° C. and a pressure of about 1000 kPa to about 5000.

16. The process of claim 1, wherein said alkene includes 1-butene and/or 2-butene, said alkylatable aromatic compound includes benzene and said alkylaromatic compound includes sec-butylbenzene.

17. The process of claim 16, wherein said conditions in (b) include a temperature of about 75° C. to about 250° C. and a pressure of about 500 kPa to about 4000 kPa.

* * * * *